United States Patent
Shevchenko et al.

(10) Patent No.: US 6,942,782 B2
(45) Date of Patent: *Sep. 13, 2005

(54) METHOD AND APPARATUS FOR MEASURING DEPOSIT FORMING CAPACITY OF FLUIDS USING AN ELECTROCHEMICALLY CONTROLLED PH CHANGE IN THE FLUID PROXIMATE TO A PIEZOELECTRIC MICROBALANCE

(75) Inventors: Sergey M. Shevchenko, Aurora, IL (US); Dmitri L. Kouznetsov, Aurora, IL (US); Prasad Y. Duggirala, Naperville, IL (US)

(73) Assignee: Nalco Company, Naperville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/127,380

(22) Filed: Apr. 22, 2002

(65) Prior Publication Data

US 2003/0070943 A1 Apr. 17, 2003

Related U.S. Application Data

(63) Continuation-in-part of application No. 09/519,688, filed on Mar. 7, 2000, now Pat. No. 6,375,829.

(51) Int. Cl.⁷ .............................. G01N 27/42
(52) U.S. Cl. .................... 205/793.5; 204/434; 205/794; 73/61.62; 73/61.75
(58) Field of Search .................... 204/433, 434; 205/793.5, 794; 73/61.62, 61.49, 580, 649, 61.75, 61.79, 64.53; 422/68.1, 69; 436/79, 6, 128

(56) References Cited

U.S. PATENT DOCUMENTS

| | | |
|---|---|---|
| 4,466,861 A | 8/1984 | Hultman et al. |
| 5,201,215 A | 4/1993 | Granstaff et al. |
| 5,233,261 A | 8/1993 | Wajid |
| 5,661,233 A * | 8/1997 | Spates et al. ............... 73/61.45 |
| 6,053,032 A | 4/2000 | Kraus et al. |
| 6,250,140 B1 | 6/2001 | Kouznetsov et al. |

FOREIGN PATENT DOCUMENTS

EP 676 637 A1 3/1995

OTHER PUBLICATIONS

CAPLUS abstract for Rosset et al, Revue des Sciences de l'Eau (1999), 12(4), pp. 753–764.*
J. Ji et al., "Surface pH measurements during nickel electrodeposition", Journal of Applied Electrochemistry, 25, 642–650 (1995).
Gabrielli et al. "Quartz Crystal Microbalance Investigation of Electrochemical Calcium Carbonate Scaling", J. Electrochem. Soc. 145, pp. 2386–2396 1998.
Khalil et al. "Water Scaling Tendency Characterization by Coupling Constant Potential Chronamperometry with Quartz Crystal Microbalance", C.R. Acad. Sci. Paris, 314, series II, pp. 145–149 (1992).

* cited by examiner

Primary Examiner—Kaj K. Olsen
(74) Attorney, Agent, or Firm—Michael B. Martin; Thomas M. Breininger (57) ABSTRACT

A method and apparatus for measuring the deposit forming propensity of a continuously flowing fluid having a bulk pH of about 1 to about 12 comprising measuring the rate at which deposit forms on a quartz crystal microbalance having a top side comprising a working electrode in contact with the fluid and a bottom side isolated from the fluid, wherein the pH of the fluid proximate to the microbalance is controlled electrochemically at about 1 to about 14 by applying to the working electrode a cathodic current of about −0.001 to about −100 mA/cm² or an anodic current of from about 0.001 to about 100 mA/cm² and wherein the working electrode is coated with or made of a conductive material on which the rate of hydrogen gas evolution is at least 10 times lower than on a gold cathode in acidic solution.

18 Claims, 4 Drawing Sheets

METHOD AND APPARATUS FOR MEASURING DEPOSIT FORMING CAPACITY OF FLUIDS USING AN ELECTROCHEMICALLY CONTROLLED PH CHANGE IN THE FLUID PROXIMATE TO A PIEZOELECTRIC MICROBALANCE

CROSS REFERENCE TO RELATED APPLICATIONS

This is a continuation-in-part of U.S. patent application Ser. No. 09/519,688, filed Mar. 7, 2000, now U.S. Pat. No. 6,375,829.

TECHNICAL FIELD

This invention relates to a method and apparatus for measuring the deposit forming propensity of fluids and the effectiveness of deposit inhibitors. More specifically, this invention concerns a method of measuring the rate of deposition on to a surface of a piezoelectric microbalance immersed in the fluid where the deposition is driven by an electrochemically controlled pH change in the vicinity of the microbalance.

BACKGROUND OF THE INVENTION

Deposit formation is a persistent problem in a variety of industrial processes involving fluids, such as pulp bleaching, sugar production and filtration. The deposits may remain suspended in the fluid or accumulate on the surface of any material that contacts the fluid. This accumulation prevents effective heat transfer, interferes with fluid flow, facilitates corrosive processes, and harbors bacteria.

A primary detrimental effect associated with such deposits is the reduction of the capacity or bore of receptacles and conduits employed to store and convey the fluid. For example, in the case of conduits used to convey scale-contaminated water, the impedance of flow resulting from deposition is an obvious consequence.

However, a number of equally consequential problems arise from utilization of deposit-contaminated fluid. For example, deposits on the surfaces of storage vessels and conveying lines for process water may break loose and become entrained in and conveyed by the process water to damage and clog equipment through which the water is passed, e.g., tubes, valves, filters and screens. In addition, these deposits may appear in, and detract from, the final product derived from the process, such as paper formed from an aqueous suspension of pulp.

Furthermore, when deposit-contaminated fluid is involved in a heat exchange process, as either the "hot" or "cold" medium, scale will be formed upon the heat exchange surfaces contacted by the fluid. Such scale formation forms an insulating or thermal opacifying barrier that impairs heat transfer efficiency as well as impeding flow through the system. Thus, deposit formation is an expensive problem in many industrial fluid systems, causing delay and expense resulting from shutdowns for cleaning and removal of the deposits.

Accordingly, there is an ongoing need for the development of new agents that prevent or inhibit the formation of deposits in fluids and for convenient methods of measuring the effectiveness of these inhibitors. In addition, as natural inhibitors may already be present in the fluids of interest, there is a need for effective methods of characterizing the tendency of industrial and biological fluids as such to form deposits.

For example, the effectiveness of scale inhibitors is manifested by their ability to suppress crystal growth through blocking active sites of potential centers of crystallization and preventing the agglomeration of growing crystals.

Common to the above processes is that they occur at the solid-fluid interface. Therefore, the in situ measurement of the deposition rate in the presence of scale inhibitors at the solid-fluid interface is of particular interest. Traditional measurements mostly relate to the change of the bulk properties of a test fluid such as solubility, conductivity, turbidity and the like following deposit formation. There exist quite a few methods for measuring deposit growth rate, however, fewer methods exist for conducting the measurements in situ at the solid-liquid interface.

Methods for measuring deposit growth rate at the solid-fluid interface that utilize a piezoelectric microbalance are disclosed in U.S. Pat. Nos. 5,201,215, and 6,250,140 and European Patent Application No. 676 637 A1. The principle of piezoelectric mass measurement is based upon the property of a quartz resonator to change its mechanical resonance frequency $f_0$ proportionally to the mass and viscoelastic properties of the deposited material. The change in frequency is expressed as follows:

$$\Delta f \approx -\frac{2f_0^2}{N(\mu_\mu \rho_q)^{\frac{1}{2}}}\left[\rho_s + \left(\frac{\rho\eta}{4\pi f_0}\right)^{\frac{1}{2}}\right]$$

where $f_0$ is the unperturbed resonant frequency of the quartz crystal; N is the harmonic number; $\mu_\mu$ is the quartz shear stiffness, $\rho_q$ is the density of quartz; $\rho_S$ is the surface mass density of the deposit (mass/area), $\rho$ is the density of the medium contacting the resonator and $\eta$ is the viscosity of the medium contacting the resonator.

Where the viscoelastic properties of the system are negligible or remain constant through the measurements, the surface mass density can be measured using a simplified expression that can be used for the loading causing the resonant frequency change up to 5% (approx. 4.5 mg/cm$^2$):

$$\rho_s = -C\,\Delta f_0$$

where C is determined by calibration and is typically equal $1.77 \times 10^{-5}$ mg/(sec cm$^2$ Hz) for a 5 MHz quartz crystal.

A method of measuring the rate of calcium carbonate scale onto the surface of the working electrode of a quartz crystal microbalance mounted in an impinging jet cell, where the working electrode is polarized using a potentiostat is disclosed in Gabrielli et al., "Quartz Crystal Microbalance Investigation of Electrochemical Calcium Carbonate Scaling", J. Electrochem. Soc., 145, 2386–2396 (1998). This method is, however, specific to calcium carbonate scale and is impractical for use in certain circumstances as a constant recirculating flow of test fluid from a reservoir through the impinging jet cell is required. Consequently, a need still exists for more flexible methods of measuring the deposit forming capacity of fluids . . .

SUMMARY OF THE INVENTION

A variety of species can be precipitated on the surface of a quartz crystal microbalance, in particular by controlling the fluid pH proximate to the surface of the microbalance by applying an appropriate current to a working electrode disposed on the surface of the microbalance. This method can be used to measure the deposit-forming propensity of any fluid where the solubility of the deposit decreases as the pH of the solution is increased or decreased.

Accordingly, in its principal aspect, this invention is directed to a method of measuring the deposit forming propensity of a continuously flowing fluid having a bulk pH of about 1 to about 12 comprising measuring the rate at which deposit forms on a quartz crystal microbalance having one side comprising a working electrode in contact with the fluid and the otherside isolated from the fluid, wherein the pH of the fluid proximate to the microbalance is controlled electrochemically from about 1 to about 14 by applying to the working electrode a cathodic current of about $-0.001$ to about $-100$ mA/cm$^2$ or an anodic current of from about $0.001$ to about $100$ mA/cm$^2$ and wherein the working electrode is coated with or made of a conductive material on which the rate of hydrogen gas evolution is at least 10 times lower than on a gold under acidic conditions.

In another aspect, this invention is directed to a method of measuring the effectiveness of deposit inhibitors comprising
a) measuring the deposit forming propensity of a continuously flowing fluid having a bulk pH of about 1 to about 12 comprising measuring the rate at which deposit forms on a quartz crystal microbalance having one side comprising a working electrode in contact with the fluid and the other side isolated from the fluid, wherein the pH of the fluid proximate to the microbalance is controlled electrochemically at about 1 to about 14 by applying to the working electrode a cathodic current from about $-0.001$ to about $-100$ mA/cm$^2$ or an anodic current from about $0.001$ to about $100$ mA/cm$^2$ and wherein the working electrode is coated with or made of a conductive material on which the rate of hydrogen gas evolution is at least 10 times lower than on a gold cathode under acidic conditions;
b) adding a deposit inhibitor to the fluid; and
c) re-measuring the rate of deposition on to the quartz crystal microbalance.

In another aspect, this invention is directed to a measurement cell for measuring the deposit forming propensity of a continuously flowing fluid having a pH of about 1 to about 12 comprising
a) a quartz crystal microbalance assembly having one side comprising a working electrode for exposure to the fluid and the other side isolated from the fluid;
b) a counter electrode in contact with the fluid for providing a uniform electric field to the microbalance; and
c) means for stirring the fluid,
wherein the pH of the solution proximate to the microbalance is controlled electrochemically at about 1 to about 14 by applying to the working electrode a cathodic current of about $-0.001$ to about $-100$ mA/cm$^2$ or an anodic current of from about $0.001$ to about $100$ mA/cm$^2$ and wherein the working electrode is coated with or made of a conductive material on which the rate of hydrogen gas evolution is at least 10 times lower than on a gold cathode under acidic conditions;

The method and apparatus of this invention is useful for benchtop laboratory work or, in a portable form, for on-site process control. The method allows reliable and prompt testing of potential deposit inhibitors in both model and real fluids. It is reproducible, sensitive and has broader applications than known techniques that suffer from interference of additional components present in industrial fluids. Specifically, this method allows for characterizing the ability of deposit inhibitors to prevent deposit growth and when used in conjunction with conventional chemical tests allows comprehensive characterization of the properties of deposit inhibitors.

In addition to testing industrial fluids, this method can be applied to biological fluids to characterize their tendency to form deposits. It has a great potential for medical applications such as urine tests for susceptibility to kidney stone formation and monitoring and screening of potential pharmaceutical remedies.

DETAILED DESCRIPTION OF THE INVENTION

This method exploits precipitation of deposits from fluids when the deposit solubility in the fluid is decreased by raising or lowering the fluid pH. As used herein, "deposit" means any organic or inorganic material that precipitates from a fluid under the conditions of pH described herein. This method is applicable to both organic and inorganic deposits, including salts of metal ions. Representative metal ions include alkaline earth metals such as sodium calcium, magnesium, and the like and transition metal ions including cadmium, cobalt, nickel, copper and the like. Typical deposits include calcium oxalate, calcium carbonate, calcium hydroxide, magnesium carbonate, magnesium phosphate, calcium uronate, calcium phosphate, cadmium carbonate, cadmium hydroxide, cobalt hydroxide, nickel hydroxide, copper hydroxide, sodium octanoate, sodium oleate, and the like.

The rate of deposit formation is measured with a sensitive quartz crystal microbalance in the vicinity of which the change in fluid pH is generated and controlled electrochemically. This method utilizes an electrochemical set-up comprising a measurement cell in which a continuous (constant for a given experimental series) flow of the test fluid is established relative to the surface of the quartz crystal microbalance (QCM). The pH of the test fluid is selected such that the deposit-forming salt is initially soluble in the test fluid but produces deposits when a change of the fluid pH is generated by applying electrochemical polarization.

The electrochemical polarization is controlled by applying anodic or cathodic current to the working electrode of the QCM. Current control is particularly advantageous compared to potential control because it does not require the use of reference electrodes and compensation for fluid resistance.

The QCM is a piezoelectric resonator connected to a measuring and driving circuit. The resonator is a quartz crystal plate with electrodes on its sides used for the connections. One of the resonator sides (the fluid side) with its electrode (the working electrode) is immersed in the test fluid and the other side (the contact side) is isolated from the fluid to avoid shunting the resonator through the fluid.

The choice of material for the working electrode is critical, as not all conductive materials are suitable under all test conditions. For example, under the acidic conditions required for the calcium oxalate tests described herein, steady production of hydrogen gas bubbles on a gold working electrode effectively hinders calcium oxalate precipitation as a result of the bubbles partially blocking the working electrode and stirring the near electrode fluid, thereby preventing the necessary pH increase. The surface of the QCM coated with a conductive material may serve as either an anode or cathode, depending on the targeted change in the surface pH.

A suitable electrode material for a given test may be determined empirically by measuring the volume of evolved hydrogen gas, or by observing the size and number of bubbles lifting off from the electrode surface under the electrochemical polarization required to precipitate the deposit from the test fluid.

For purposes of this invention the working electrode may made of or coated with any chemically stable, conductive material on which the rate of hydrogen evolution is at least 10 times lower than on gold cathode under the required conditions of solution pH and electrochemical polarization in an acidic solution. Other considerations in selecting the electrode material include simplicity of handling, cost, and resistance to dissolution during the test. For a detailed description of the dependence of exchange current density for the hydrogen evolution reaction on the strength of the metal-hydrogen bond formed in an electrode reaction see D. Pletcher and F. Walsh, "Industrial Electrochemistry" Blackie Academic and Professional, London, 1993.

Preferred conductive materials include gold, titanium; silver; lead; cadmium; diamond-like thin film electrodes with or without implanted ions; silicon, silicides of titanium, niobium and tantalum; lead-selenium alloys; and mercury amalgams, and the like.

Under test conditions where anodic current is applied to the electrode, the conductive material must withstand the resulting oxidative conditions. Preferred electrode materials for this application include titanium, diamond-like thin film electrodes, silicon, silicides of titanium, niobium, tantalum, and the like.

Figure 6:
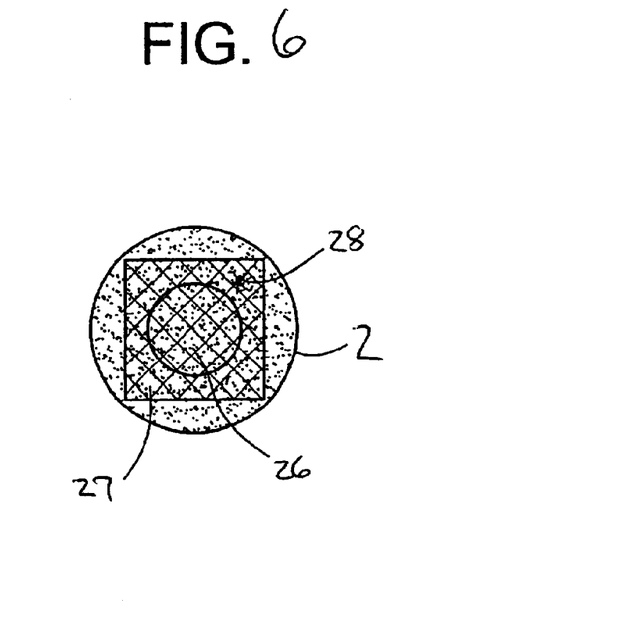
FIG. 6 is a top plan view of the surface pH measuring module (2).
Figure 7:
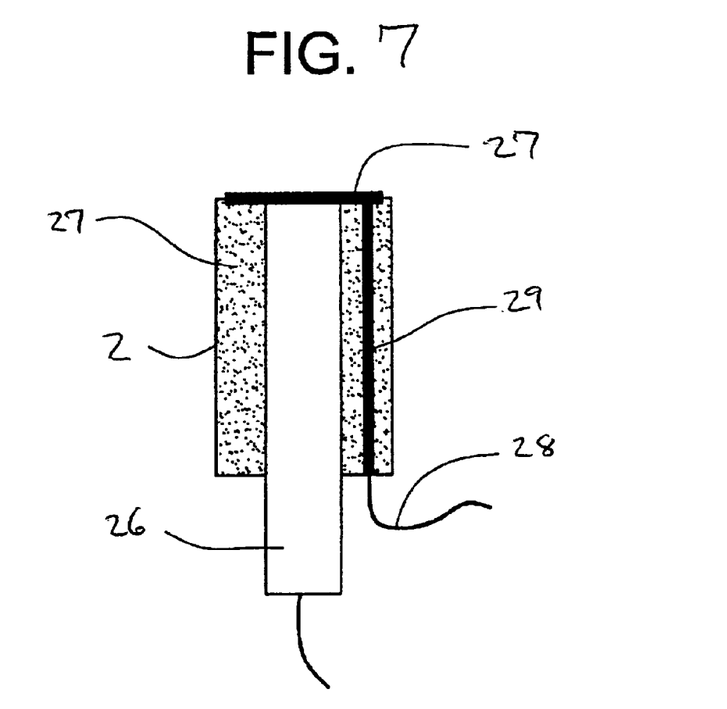
FIG. 7 is a cut away view of the surface pH measuring module (2).

In an embodiment of this invention, the pH measurement is accomplished using a surface pH-measuring module (2) comprising a mesh electrode (27) laid over a flat-tip combination pH electrode (26) as shown in FIGS. 6 and 7. The mesh should be as thin and dense as possible and made of the same material as the microbalance working electrode. Once subjected to the same test conditions, the mesh electrode allows approximating the surface pH conditions near the microbalance surface.

In another embodiment, the pH measurement is accomplished using a microtip combination electrode such as those available from Microelectrodes, Inc., Bedford, N.H. A microtip combination electrode is a miniaturized conventional pH electrode based on selective diffusion of protons though hydrogen ion sensitive glass, and the determination of potentials between the internal electrolyte and a silver/silver chloride reference electrode.

In another embodiment, the surface pH measurement is accomplished using a pH electrode fabricated on the fluid side of the quartz crystal microbalance (1). The working electrode (16) of the microbalance (1) has definite dimensions. The geometry of the electrochemical diffusion layer near the edge of this electrode presumes that the electrochemically induced pH change occurs not only in the vicinity above the electrode but also near the electrode edge in the lateral direction in the same plane. Therefore, if a small size pH sensor is placed near the edge and in the same plane as the microbalance working electrode the measurement of the near electrode pH is possible.

Thin-film metal oxide electrodes are preferred for such pH measurements. These materials are prepared by reactive sputtering of metals selected form the group of tungsten, platinum, palladium, ruthenium, and iridium metal targets in argon-oxygen atmospheres to produce a thin film several micron thick directly on the quartz crystal substrate (17).

As described above, the rate of precipitation of a deposit is measured by precipitating the deposit on to the QCM in the vicinity of which a change in fluid pH is generated and controlled electrochemically. Control of the pH is accomplished using a surface pH measuring module. The module serves to establish the dependence of the near electrode pH on applied electrochemical polarization at given test conditions.

A slow scan of current from a near zero to a sufficiently large current densities (typically about 30 mA/cm2) is used to determine the current ranges producing the desired increase or decrease in pH. Consequently, the current is controlled in this range during the scale deposition. Once the appropriate current is established for a certain class of fluids, this value is used in all further experiments without performing additional pH scans. For example, calcium oxalate at bulk pH 2.5 requires current density of 4.5 mA/cm$^2$ in a model 1 mM solution and 5 mA/cm$^2$ in pulp mill bleaching effluents; calcium carbonate at bulk pH 7.8 requires current density of 4.5 mA/cm$^2$ in pulp mill bleaching effluents.

Test conditions and representative electrode materials for a variety of scale-forming salts are summarized in Table 1. In Table 1, "Bulk pH" refers to the test solution pH, "Proximate pH" refers to the pH proximate to the working electrode of the QCM and "Current density" refers to the current density applied to the working electrode in order to generate the proximate pH.

TABLE 1

| Inorganic Salt | Bulk pH | Proximate pH | Current Density (mA/cm$^2$) | Electrode Material |
| --- | --- | --- | --- | --- |
| Calcium Oxalate | 2.4–2.7 | 5–9 | −4.5 to −6 | Ag |
| Calcium Oxalate | 1.8 | 2.5 | −25 | Ag |
| Calcium Carbonate | 7–8 | 10.5–12 | −4 to −6 | Au |
| Calcium hydroxide (from hydrocarbonate) | 9–10 | 13–14 | −5 to −6 | Au, Ti |
| Magnesium Carbonate | 7–8 | 10.5–12 | −4 to −6 | Au |
| Magnesium phosphate | 2–3 | 7–10 | −6 to −7.5 | Ag |
| Calcium uronate | 2.4–2.7 | 5–9 | −4.5 to −6 | Ag, Ti |
| Calcium phosphate | 2–3 | 7–10 | −6 to −7.5 | Ag$^+$ |
| Cadmium carbonate | 7–8 | 11–12 | −5 to −6.5 | Au |
| Cadmium hydroxide (from hydrocarbonate) | 9–10 | 13–14 | −5 to −7.5 | Ti |
| Cobalt hydroxide (from chloride) | 6–7 | 12–13 | −7.5 to −11 | Ti |
| Nickel hydroxide (from chloride) | 6–7 | 12–13 | −7.5 to −11 | Ti |
| Copper hydroxide (from chloride) | 6–7 | 12–13 | −7.5 to −11 | Ti |
| Sodium octanoate (free acid deposits) | 10–11 | 5–6 | +4 to +7.5 | Ti, diamond-like thin films |
| Sodium oleate | 10–11 | 5–6 | +4 to +7.5 | Ti, diamond-like thin films |

In a preferred aspect of this invention, the deposit is calcium carbonate.

A preferred working electrode material for measuring the calcium carbonate scaling capacity of a solution is gold.

In another preferred aspect, the calcium carbonate solution has a bulk pH of about 7 to about 8 and the pH of the solution proximate to the microbalance is controlled electrochemically at about 10.5 to about 12 by applying to the working electrode a cathodic current of from about −4.5 to about −6 $mA/cm^2$.

In another preferred aspect, the deposit is calcium oxalate.

A preferred working electrode material for measuring the calcium oxalate scaling capacity of a solution is silver or titanium. A more preferred electrode material is titanium.

Use of titanium allows accumulation of calcium oxalate deposit with less hydrogen evolution than a silver working electrode. Moreover, the titanium coating is more chemically and electrochemically resistant and allows for a reverse of current that makes a QCM an anode. Such a reverse is not recommended for a silver-coated QCM since it leads to immediate corrosion of the metal layer. A reverse of current allows for an electrochemical cleaning of the QCM working electrode after a deposition experiment. Reversing the current to make the QCM an anode results in rapid dissolution of calcium oxalate deposited on the surface of the QCM thus making it possible to clean the system between experiments without disassembling it. This option is of special importance for on-line applications of the technique.

In another preferred aspect, the calcium oxalate solution has a bulk pH of about 1.5 to about 2 and the pH of the solution proximate to the microbalance is controlled electrochemically at about 2 to about 5 by applying to the working electrode a cathodic current of from about −5 to about −30 $mA/cm^2$.

Figure 1:
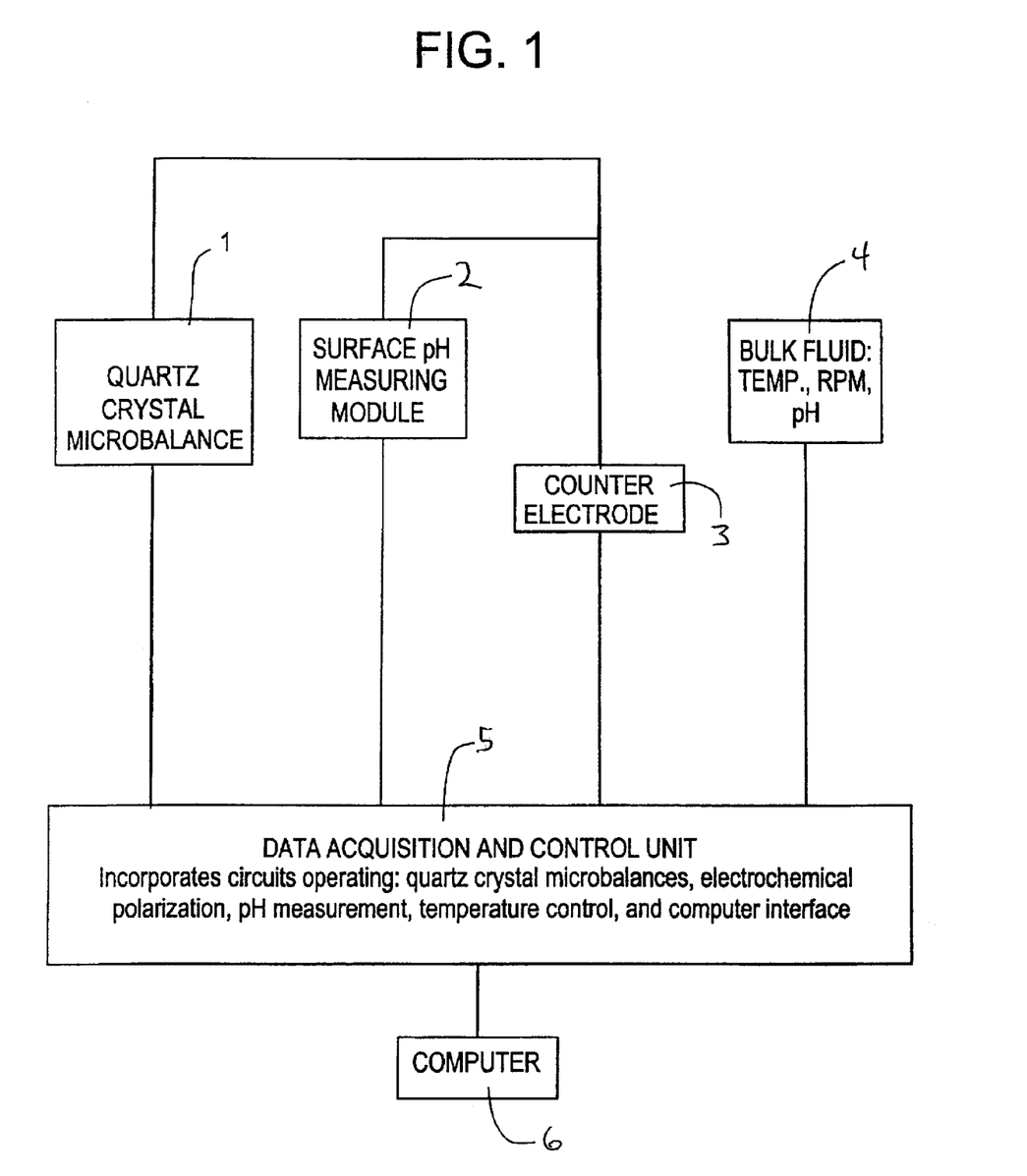
FIG. 1 is a block diagram of an apparatus of this invention.
Figure 2:
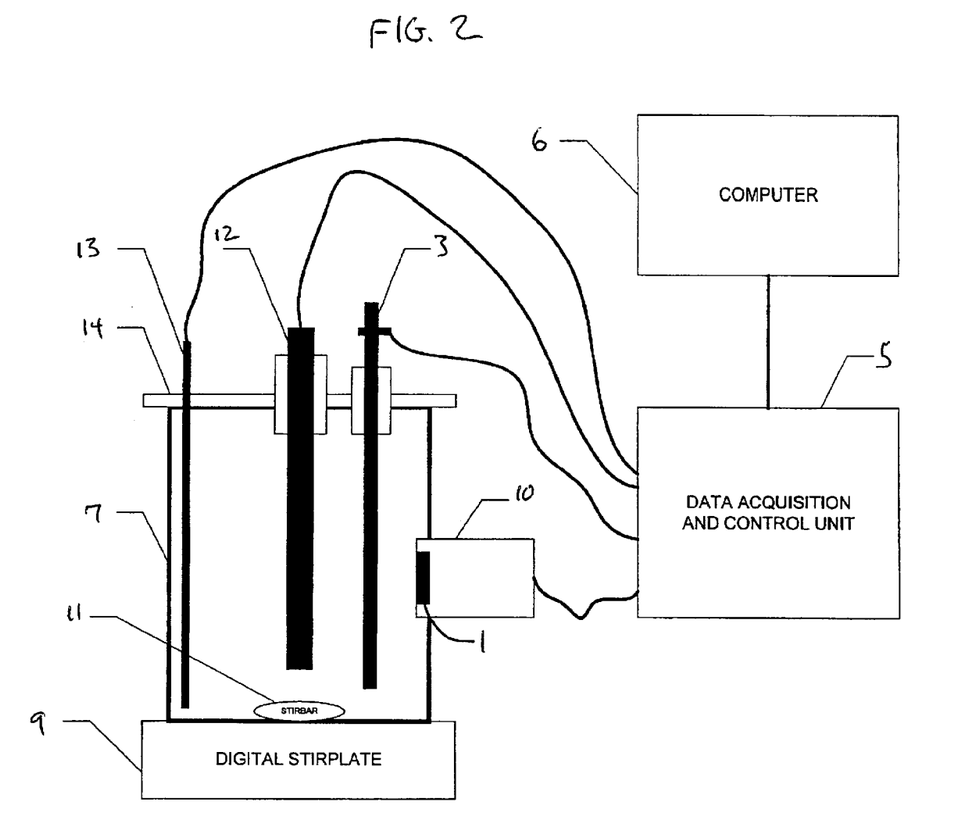
FIG. 2 is a schematic diagram of a preferred configuration of the apparatus of this invention.

Embodiments of the apparatus of this invention is shown in FIGS. 1 and 2. The apparatus consists of a quartz crystal microbalance (1), a surface pH measuring module (2), counter electrode (3), means (4) for controlling and measuring bulk fluid temperature, fluid flow and pH, and a data acquisition and control unit (5) connected to an external computer (6).

The data acquisition and control unit (5) executes experimental procedures and relays the experimental data to an external computer (6). The computer software controls the experiment setup and data acquisition, and processes and plots the data. The programmed parameters are: applied current, temperature, stirring rate, time of the experiment and readings per minute. Other parameters are programmed via the software operating the apparatus from a computer. The external computer processes and stores the experimental data while displaying the test parameters and the deposition graphs (deposited mass and rate) in real time. It also monitors the actual current in the system and frequency of the microbalance. The collected data can also be compiled and analyzed immediately using commercially available data analysis software. The temperature and stirring rate are programmed separately via respective devices (the temperature controller and digitally controlled stirring means).

The measurement cell (7) is configured in a two-electrode arrangement using the working electrode (16) of the quartz crystal microbalance (1) and counter electrode (3). The measurement cell is made of chemically resistant plastic, preferably transparent (e.g., PVC or/and acrylic).

The counter electrode (3) is electrolytically connected to the bulk fluid and capable of applying a uniform electric field to the working electrode of the microbalance (1). The counter electrode (3) is manufactured from graphite or other resistant materials readily apparent to those of skill in the art such as platinum, stainless steel, and the like.

In principle, the apparatus of this invention can utilize any electric source capable of supplying to the working electrode a polarization of suitable magnitude, polarity and stability. The electrical conditions established in the circuits can be controlled and measured using the equipment commonly used by those skilled in the art.

A steady flow of the bulk liquid past the quartz crystal microbalance (1) is accomplished using a suitable stirring device such as an impeller, a mechanical paddle stirrer, or a magnetic stirbar. In the preferred embodiment, a magnetic stirbar (11) and digitally controlled stirplate (9) are used. By "steady," a relatively constant flow is intended. That optimal flow rate can be readily determined in an experiment on a model fluid. The preferred rate for the unit displayed in FIG. 2 is 400 rpm.

The temperature of the fluid is controlled using any suitable thermal regulating means including, but not limited to, a cooler or heater (12) disposed in the bulk liquid. The temperature of the bulk liquid is measured by a thermocouple (13) connected to a controller. The temperature of the bulk liquid as measured by the thermocouple can be maintained constant or be varied, as much as is practical to simulate the desired system.

The apparatus of this invention is operated as a batch system as shown in FIG. 2. In FIG. 2, number (10) represents a position in the measurement cell (7) at which either a surface pH measuring module (2) or the quartz crystal microbalance assembly (15) can be attached to the measurement cell (7). A removable cover (14) for the measurement cell contains apertures for the cooler or heater (12), temperature sensor (13) and counter electrode (3).

Initially, optimal pH conditions are determined with the surface pH measuring module (2) installed. Then the surface pH measuring module is removed and the quartz microbalance assembly (15) is installed for measurement of scale forming capacity. In the first case, the mesh electrode (32) of the surface pH module (2) is connected to the same electrochemical system and subjected to the same test conditions as the working electrode (16) of microbalance (1). Both surface and bulk pH in the system are measured using the surface pH measuring module (2) connected to a pH-reading circuit in the data acquisition and control unit (5).

Figure 3:
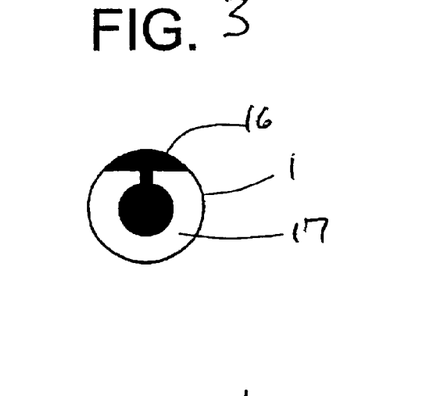
FIG. 3 is a top plan view of the quartz sensor of the quartz crystal microbalance (1).
Figure 4:
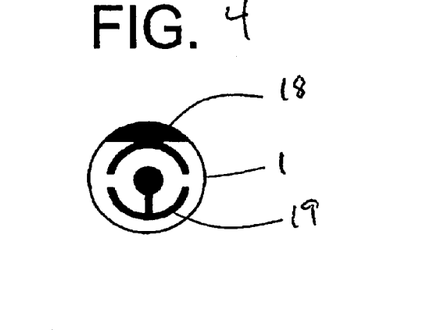
FIG. 4 is a bottom plan view of the quartz sensor of the quartz crystal microbalance (1).
Figure 5:
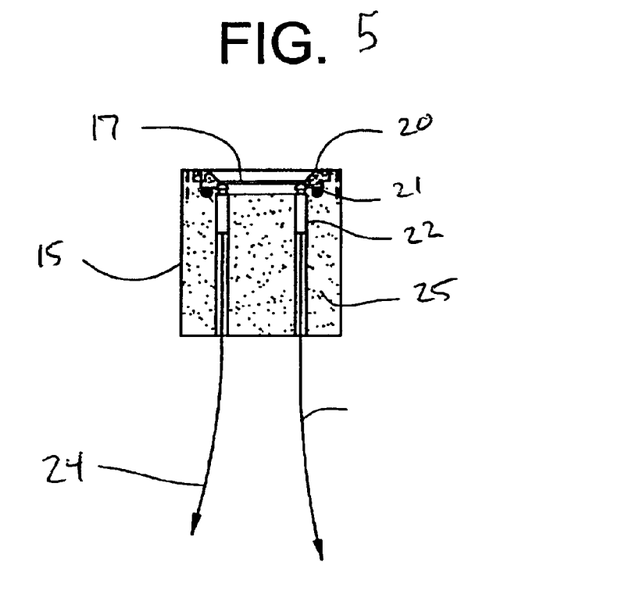
FIG. 5 is a cut away view of the quartz crystal microbalance assembly (15).

Preferred configurations of the quartz crystal microbalance (1) and quartz crystal microbalance assembly (15) are shown in FIGS. 3–5. In this embodiment, the mass sensing element of the piezoelectric microbalance is an AT cut quartz crystal (17) with evaporated electrodes (16), (18), and (19). Electrode (16) is the working electrode as it is immersed into the tested fluid during measurements.

Working electrode (16) wraps around the edge of the top or fluid side of the crystal (17) to its bottom side to form contact (18) as shown in FIG. 4. The bottom side of the quartz crystal (17) includes contact (18) and second contact (19). Contacts (18) and (19) provide electrical connections with the microbalance operating circuit in the data acquisition and control unit (5) by way of connecting wires.

The quartz crystal microbalance assembly (15) is shown in FIG. 5. The quartz crystal (17) is sealed in an aperture of a plastic cylinder (25). A retainer ring (20) and at least one O-ring (21) ensure that only the top side of the quartz crystal (17) is exposed to the test fluid and that the bottom side of the crystal is isolated from the fluid. Spring-loaded contacts (22) operatively connect the connecting leads (23) and (24) respectively to the working electrode (16) and contact (19). The leads are then connected to the microbalance operating circuit in the data acquisition and control unit (5).

The top or fluid side of the preferred surface pH measuring module (2) of this invention is shown in FIGS. 6 and 7. In this embodiment, a flat-bottom, upside-down mountable combination pH electrode (26) is fixed coaxially in a plastic cylinder (27) in such a way that the flat sensing surface of the electrode is in direct contact with a mesh (27) made of the same material as the microbalance electrode (16) and attached to the top of the plastic cylinder.

Maximizing the number of apertures per inch in mesh (27) leads to a better simulation of the microbalance working electrode. Variation of this parameter can be achieved by using mesh as thin and dense as practically available.

As shown in FIG. 7, the flat mesh (27) is connected to the electrochemical circuit in the data acquisition and control unit (5) using a wire (28) passing through an eccentric channel (29) in the plastic cylinder (27). Both the wire (28) and pH electrode (26) are tightly sealed in the corresponding channels of cylinder (27). The pH electrode (26) is connected to the pH reading circuits in the data acquisition and control unit. With the thickness of mesh (27) less than the electrochemical diffusion layer the device allows measuring the pH near the polarized electrode surface, thus simulating the environment near the surface of the working quartz microbalance. The same polarization is applied to the mesh electrode (27) of the surface pH module (2) and the working electrode of the quartz microbalance (1).

The foregoing may be better understood by reference to the following Examples that are presented for purposes of illustration and are not intended to limit the scope of this invention.

EXAMPLES

The use of the method and apparatus of this invention to measure the effectiveness of calcium oxalate and calcium carbonate scale inhibitors in Kraft pulp bleach plants is described below. It is understood that the following is illustrative of applications of this invention and is not intended to be limiting.

Pulp produced by the Kraft process is normally bleached in a multistage sequence to obtain the desired brightness and strength. The main objectives of pulp bleaching are to increase the brightness of the pulp and to make it suitable for the manufacture of printing and tissue grade papers by removal or modification of lignin and its degradation products of the unbleached pulp. The bleaching of chemical pulp is accomplished by a series of treatments involving chlorine dioxide, caustic, hydrogen peroxide, and other bleaching agents. The bleaching of chemical pulp normally begins with the first stage chlorine dioxide. The bleaching of pulp is done through chemical reactions of bleaching agents with the lignin and coloring matter of the pulp under different conditions of temperature, time, concentration, and pH.

Calcium oxalate and calcium carbonate scale present a difficult problem to control that can impair the performance of stock pipelines, washing filters, filtrate tanks, refiner plates, and heat exchangers. The formation of these deposits is a result of relatively high concentration of calcium oxalate in process equipment operating in the pH range of 2–8 and calcium carbonate in process equipment operating in the pH range of 9–11. The removal of these materials is difficult and results in costly downtime.

The source of calcium oxalate in pulp bleaching operations is ultimately due to the wood. Calcium is introduced into the pulp mill principally from the wood, although some calcium may also be introduced into the process from the mill's fresh water and cooking liquor (sodium hydroxide and sodium sulfide). Oxalic acid is formed during pulping and bleaching but is also present in native wood. Carbon dioxide from the air reacts with alkaline mill solutions producing carbonate and hydrocarbonate ions that creates potential for calcium carbonate deposition. The precipitation of calcium oxalate and calcium carbonate is strongly dependent upon changes in temperature and pH.

In the batch system, the microbalance and counter electrode are installed in the proximity to each other (from about 1 to about 3 cm). The length of the counter electrode is such that it passes through the cell top to bottom but still allows for stirbar rotation. A high-density graphite counter electrode (Perkin-Elmer, Oak Ridge, Tenn.) is used. The apparatus is designed to be used with 1-L samples. The measurement cell is made of Plexiglas. The quartz microbalances used are 5 MHz silver- or titanium-coated polished quartz crystals (Maxtek, Inc., Torrance, Calif.). In calcium carbonate tests, gold-coated crystals can also be used. A digitally controlled 400S Stirrer and Teflon-coated 62-mm Spinstar stirbar (VWR, Chicago, Ill.) are used. The systems are connected to data acquisition and control unit.

The data acquisition and control unit is a microprocessor-controlled electronic instrument that incorporates circuits operating the quartz crystal microbalance and electrochemical galvanostat. The unit is connected to an external computer. The computer software controls the experiment setup and data acquisition and processing. The programmed parameters are: applied current, temperature, and stirring rate of the solution. The bulk pH of the solution is adjusted as fit for each type of the tests. The computer software processes and stores the experimental data while displaying the test parameters and the deposition graphs (deposition amount and rate) in real time. In a preferred apparatus, an Omega CN76000 microprocessor-based temperature controller is integrated into the apparatus to maintain the desired temperature of the solution.

The measurements for calcium oxalate are performed at 25° C. and bulk pH 2.5–2.7. The measurements for calcium carbonate are performed at 25° C. or 70° C. and bulk pH 7.8–8.0. Stirbar rotation speed of 400 rpm is maintained.

The scaling capacity of a solution is evaluated by the deposition rate observed at preset time intervals as well as by the total deposited mass accumulated by the end of the test. The percent inhibition is calculated as follows:

% Inhibition=100%×(Total deposit w/o inhibitor−Total deposit with inhibitor)/Total deposit without inhibitor.

In Tables 1–2, Samples A and A1 is a terpolymeric organic acid of different degree of polymerization. Sample B is an alkaline solution of an acrylic polymer with a small amount of sulfur-containing inorganic salts. Sample C is a mixture of an acrylic polymer with an inorganic phosphorous salt. Composition D is a carbohydrate-based inhibitor. Sample E is a phosphonate polymer. Compositions A–D are available from Ondeo Nalco Chemical Company, Naperville, Ill.

Example 1
Screening Of Calcium Oxalate Scale Inhibitors Using Model Solutions

A 1-mM (128-ppm) test solution of calcium oxalate is prepared as follows. Sodium oxalate (0.268 g) and calcium chloride dihydrate (0.294 g) are separately dissolved in 35 ml of 0.1 N HCl. The solutions are diluted to 100 ml each with deionized water, mixed under intense stirring, and the mixed solution is diluted to 2 L volume with deionized water with 0.1 N HCl added as needed to adjust the pH to 2.6. This solution is used as the control. The rest of the solutions contained a potential inhibitor. The results are given in Table 2.

TABLE 2

Results of inhibitor screening in model solution (1 mM calcium oxalate)

| Test solutions | Deposition rate, mg/cm2/hour at reference time periods | | | Total deposited mass, mg/cm$^2$ | % Inhibition |
|---|---|---|---|---|---|
| | 10 min | 20 min | 30 min | 30 min | |
| Control, 1 mM calcium oxalate | 0.38 | 0.45 | 0.43 | 0.15 | |
| A, 10 ppm actives | 0.10 | 0.14 | 0.18 | 0.03 | 80.8 |
| A, 40 ppm actives | 0.08 | 0.08 | 0.10 | 0.002 | 98.6 |
| B, 10 ppm actives | 0.22 | 0.36 | 0.44 | 0.11 | 28.1 |
| C, 10 ppm actives | 0.13 | 0.17 | 0.18 | 0.04 | 76.7 |

Example 2

Dependence of Mass Accumulation of Calcium Oxalate Scale on the Applied Current Density Applied on Titanium Coated QCM The results are given in Table 3. A 1-mM (128-ppm) test solution of calcium oxalate at bulk pH 2.4 is used in this test. After calcium oxalate is deposited on the surface of the QCM, the current is reversed (applied current density +2.0 mA/cm$^2$). Rapid mass loss due to dissolution of calcium oxalate is observed, with no damage to the QCM.

TABLE 3

Results Of Calcium Oxalate Mass Accumulation from Model Solution on Titanium Coated QCM (1-mM calcium oxalate).

| Applied current density, mA/cm$^2$ | Deposited mass, mcg/cm$^2$ at reference time periods | | |
|---|---|---|---|
| | 5 min | 10 min | 15 min |
| 5 | 0.6 | 1.5 | 21.4 |
| 7.5 | 1.4 | 4.1 | 60.6 |
| 11 | 2.5 | 8.1 | 100.8 |
| 22 | | 25.8 | 207.2 |

Example 3

Screening of Calcium Oxalate Scale Inhibitors Under Acidic Conditions in Model Solutions 4-mM (128-ppm) supersaturated solutions of calcium oxalate at bulk pH 1.8 are used in this test. The inhibitors (20-ppm concentration based on the dry weight) are added prior to mixing equimolar calcium chloride and sodium oxalate solutions. An estimate obtained with a surface pH probe used consecutively indicates that the applied current of 22 mA/cm$^2$ leads to a pH increase to 2.5–3.0. The results are given in Table 4.

TABLE 4

Results of inhibitor screening in model solution (4 mM calcium oxalate)

| Test solutions | Deposited mass, mcg/cm$^2$ at reference time periods | | |
|---|---|---|---|
| | 10 min | 15 min | 20 min |
| Control, 4 mM calcium oxalate | 105 | 310 | |
| A, 20 ppm actives | 65 | 265 | |
| C, 20 ppm actives | 10 | 20 | 75 |
| D, 20 ppm actives | 13 | 35 | 100 |

Example 4

Screening of Calcium Oxalate Scale Inhibitors Using Mill Water

The test solutions contain 1-mM (128-ppm) of calcium oxalate added to mill water. Sodium oxalate (0.107 g) and calcium chloride dihydrate (0.118 g) are separately dissolved in 400-ml of mill water. 0.1 N HCl is added to the samples to maintain pH at about 2.5. The solutions are mixed and used as the control without an inhibitor, or with inhibitors for screening.

The system is flushed with deionized water immediately after the analysis. After each analysis of model solution or mill water, the surface of the crystal is cleaned of the deposit with 0.1 N HCl (5–10 min) and washed with deionized water. The results are given in Table 5.

TABLE 5

Results Of Inhibitor Screening in Mill Water (1-mM Calcium Oxalate Added)

| Test solutions | Deposition rate, mg/cm2/hour at reference time periods | | | | Total deposited mass, mg/cm$^2$ | % Inhibition |
|---|---|---|---|---|---|---|
| | 10 min | 20 min | 30 min | 40 min | 40 min | |
| Control, Mill water + 1 mM calcium oxalate | 0.49 | 0.58 | 0.5 | 0.39 | 0.261 | |
| A, 10 ppm actives | 0.10 | 0.10 | 0.11 | 0.10 | 0.010 | 96.2 |
| D, 10 ppm actives | 0.12 | 0.13 | 0.14 | 0.13 | 0.035 | 86.6 |

The experimental data summarized in Tables 2, 4, and 5 clearly distinguish more and less effective inhibitor compositions. Thus, composition A decreases the rate of deposition dramatically and is the most effective in both mill water and in model solutions.

Example 5
Screening of Calcium Oxalate Scaling Capacity of Mill Waters Acquired from Various Hardwood D0 Process Stages The results of the use of the apparatus for screening of the oxalate scaling capacity of actual mill waters acquired from various D0 process stages are given in Table 6. Two sets of mill water, taken before and after the change in the operational procedure at the mill, were analyzed. The tests were performed on the original solutions and on the same solutions spiked with 1-mM calcium oxalate.

TABLE 6

Scaling Capacities of Mill Waters

| Test solutions | Deposition rate, mg/cm2/hour at reference time periods | | | | Deposited mass, mcg/cm$^2$ at reference time periods |
|---|---|---|---|---|---|
| | 10 min | 20 min | 30 min | 40 min | 40 min |
| Mill Water 1, pH 2.46 (before procedure change), no calcium oxalate | 0.08 | 0.11 | 0.10 | 0.10 | 0.026 |
| Mill Water 1, pH 2.46 (before procedure change) + 1 mM calcium oxalate | 0.51 | 0.75 | 0.90 | 1.00 | 0.425 |
| Mill Water 2, pH 2.25 (after procedure change) | 0.09 | 0.09 | 0.10 | 0.12 | 0.011 |
| Mill Water 2, pH 2.25 (after procedure change) + 1 mM calcium oxalate | 0.48 | 0.65 | 0.67 | 0.70 | 0.332 |

Example 6
Screening of Calcium Carbonate Scaling Capacity of Mill Waters Acquired from Hardwood D0 Process Stage (Gold Coated QCM)

The test results of the calcium carbonate scaling capacity of D0 filtrate are given in Table 7. The pH of the sample is adjusted to 8.0 and 100 ppm of sodium carbonate were added, and current density 5.0 mA/cm$^2$ was applied. The samples contained scale inhibitors A and E at different concentrations. The test demonstrates the effect of the inhibitor concentration on the scaling capacity of the solution.

TABLE 7

Scale Capacities of Mill Waters

| Sample | Deposited mass, mcg/cm$^2$ at reference time periods | | |
|---|---|---|---|
| | 5 min | 10 min | 15 min |
| No additives | 56 | 107 | 162 |
| Inhibitor E, 1 lb./t | 47 | 89 | 136 |

TABLE 7-continued

Scale Capacities of Mill Waters

| Sample | Deposited mass, mcg/cm$^2$ at reference time periods | | |
|---|---|---|---|
| | 5 min | 10 min | 15 min |
| Inhibitor E, 2 lb./t | 38 | 73 | 110 |
| Inhibitor E, 3 lb./t | 29 | 55 | 83 |
| Inhibitor A, 3 lb./t | 21 | 40 | 60 |

Example 7
Screening of Calcium Carbonate/Magnesium Carbonate Scale Inhibitors using Gold Coated QCM The pH of the sample (magnesium oxide slurry diluted 1:400) was adjusted to 8.0, and current 4.5 mA/cm$^2$ was applied. The results are given in Table 8.

TABLE 8

Results Of Calcium Oxalate/Magnesium Carbonate Mass Accumulation From Magnesium Oxide Slurry In The Presence Of 40 ppm Inhibitor.

| Inhibitor | Deposited mass, mcg/cm$^2$ at reference time periods | |
|---|---|---|
| | 5 min | 10 min |
| None | 33 | 75 |
| A | 5 | 10 |
| B | 13 | 30 |

Although this invention has been described in details for the purpose of illustration, it is to be understood that such details are provided solely for that purpose and that numerous modifications, alterations and changes can be made therein by those skilled in the art without departing from the spirit and scope of the invention except as it may be limited by the claims. All changes which come within the meaning and range of equivalency of the claims are to be embraced within their scope.

What is claimed is:

1. A method of measuring the deposit forming propensity of a continuously flowing fluid having a bulk pH of about 1 to about 12 comprising measuring the rate at which deposit forms on a quartz crystal microbalance having a top side comprising a working electrode in contact with the fluid and the other side isolated from the fluid, wherein the pH of the fluid proximate to the microbalance is controlled electrochemically, via a galvanostatic system, at about 1 to about 14 by applying to the working electrode a cathodic current of about −0.001 to about −100 mA/cm$^2$ or an anodic current of from about 0.001 to about 100 mA/cm$^2$ and wherein the working electrode is coated with or made of a conductive material on which the rate of hydrogen gas evolution is insufficient to hinder precipitation of scale onto the working electrode under the electrochemical polarization required to precipitate the deposit from the fluid.

2. The method of claim 1 wherein the working electrode is made of or coated with one or more conductive materials selected from gold, titanium, silver; lead; cadmium; diamond-like thin film electrodes with or without implanted ions; silicon, silicides of titanium, niobium and tantalum; lead-selenium alloys; and mercury amalgams.

3. The method of claim 1 wherein the deposit is selected from the group consisting of calcium oxalate, calcium carbonate, calcium hydroxide, magnesium carbonate, magnesium phosphate, calcium uronate, calcium phosphate, cadmium carbonate, cadmium hydroxide, cobalt hydroxide, nickel hydroxide, copper hydroxide, sodium octanoate and sodium oleate.

4. The method of claim 1 wherein the pH of the fluid proximate to the surface of the microbalance is measured using a surface pH-measuring module comprising a mesh electrode laid over a pH electrode wherein the mesh is made of the same material as the working electrode.

5. The method of claim 1 wherein the pH of the fluid proximate to the surface of the microbalance is measured using a pH-measuring device selected from a microtip pH electrode and a pH electrode fabricated on the surface of the quartz crystal microbalance.

6. The method of claim 1 wherein the deposit is calcium carbonate.

7. The method of claim 6 wherein the working electrode is made of gold.

8. The method of claim 7 wherein the fluid has a bulk pH of about 7 to about 8 and wherein the pH of the fluid proximate to the microbalance is controlled electrochemically at about 10.5 to about 12 by applying to the working electrode a cathodic current of from about −4.5 to about −6 mA/cm$^2$.

9. The method of claim 1 wherein the deposit salt is calcium oxalate.

10. The method of claim 9 wherein the working electrode is made of silver, titanium, diamond like thin films, silicon, suicides of titanium, niobium and tantalum.

11. The method of claim 10 wherein the fluid has a bulk pH of about 1.5 to about 2 and wherein the pH of the fluid proximate to the microbalance is controlled electrochemically at about 2 to about 5 by applying to the working electrode a cathodic current of from about −5 to about −30 mA/cm$^2$.

12. A method of measuring the effectiveness of deposit inhibitors comprising
 a) measuring the inorganic scale forming propensity of a continuously flowing solution having a bulk pH of about 1 to about 12 comprising measuring the rate at which deposit forms on a quartz crystal microbalance having a top side comprising a working electrode in contact with the solution and a bottom side isolated from the solution, wherein the pH of the solution proximate to the microbalance is controlled electrochemically, via a galvanostatic system, at about 1 to about 14 by applying to the working electrode a cathodic current of about −0.001 to about −100 mA/cm$^2$ or an anodic current of from about 0.001 to about 100 mA/cm$^2$ and wherein the working electrode is coated with or made of a conductive material on which the rate of hydrogen gas evolution is insufficient to hinder precipitation of scale onto the working electrode under the electrochemical polarization required to precipitate the deposit from the fluid;
 b) adding a deposit inhibitor to the solution; and
 c) re-measuring the rate of deposition on to the quartz crystal microbalance.

13. A measurement cell for measuring the deposit forming propensity of a continuously flowing solution having a pH of about 1 to about 12 comprising
 a) a quartz crystal microbalance assembly having a top side comprising a working electrode for exposure to the fluid and a bottom side isolated from the fluid; or
 b) a surface pH-measuring module for exposure to the fluid, the pH-measuring electrode assembly comprising a mesh electrode laid over a pH electrode wherein the mesh is made of the same material as the working electrode of the microbalance;
 c) a counter electrode in contact with the fluid for providing a uniform electric field to the microbalance; and
 d) means for stirring the fluid,
 wherein the pH of the solution proximate to the microbalance is controlled electrochemically at about 1 to about 14 by applying to the working electrode a cathodic current of about −0.001 to about −100 mA/cm$^2$ or an anodic current of from about 0.001 to about 100 mA/cm$^2$, wherein the working electrode is coated with or made of a conductive material on which the rate of hydrogen gas evolution is insufficient to hinder precipitation of scale onto the working electrode under the electrochemical polarization required to precipitate the deposit from the fluid and wherein optimal pH conditions are determined with the surface pH module installed and scale forming capacity is measured with the quartz crystal microbalance assembly installed.

14. The measurement cell of claim 13 further comprising means for monitoring and controlling the temperature of the fluid.

15. The measurement cell of claim 14 wherein the means for monitoring and controlling the temperature of the fluid are immersed in the fluid.

16. The measurement cell of claim 13 wherein the quartz crystal microbalance assembly or surface pH measuring module is disposed horizontally in the measurement cell and the counter electrode is disposed vertically and downstream from the quartz crystal.

17. The apparatus of claim 13 wherein the working electrodes of the quartz crystal microbalance assembly is made of or coated with one or more conductive materials selected from gold, titanium, silver; lead; cadmium; diamond-like thin film electrodes with or without implanted ions; silicon, silicides of titanium, niobium and tantalum; lead-selenium alloys; and mercury amalgams.

18. A measurement cell for measuring the deposit forming propensity of a continuously flowing solution having a pH of about 1 to about 12 comprising
 a) a quartz crystal microbalance assembly having a top side comprising a working electrode for exposure to the fluid and a bottom side isolated from the fluid;
 b) a surface pH-measuring module for exposure to the fluid, the pH-measuring electrode assembly comprising a mesh electrode laid over a pH electrode wherein the mesh is made of the same material as the working electrode of the microbalance;
 c) a counter electrode in contact with the fluid for providing a uniform electric field to the microbalance; and
 d) means for stirring the fluid,
 wherein the pH of the solution proximate to the microbalance is controlled electrochemically at about 1 to about 14 by applying to the working electrode a cathodic current of about −0.001 to about −100 mA/cm$^2$ or an anodic current of from about 0.001 to about 100 mA/cm$^2$ and wherein the working electrode is coated with or made of a conductive material on which the rate of hydrogen gas evolution is insufficient to hinder precipitation of scale onto the working electrode under the electrochemical polarization required to precipitate the deposit from the fluid.

* * * * *